United States Patent [19]

Biselli et al.

[11] Patent Number: 5,601,757
[45] Date of Patent: Feb. 11, 1997

[54] GASIFICATION-TUBE MODULE AND REACTOR FOR CELL CULTIVATION

[75] Inventors: Manfred Biselli, Jülich; Christoph Born, Aachen; Bernd Scröder; Christian Wandrey, both of Jülich, all of Germany

[73] Assignee: Forschungszentrum Julich GmbH, Julich, Germany

[21] Appl. No.: 517,008

[22] Filed: Aug. 18, 1995

[30] Foreign Application Priority Data

Aug. 24, 1994 [DE] Germany .............................. 9413575 U
Aug. 24, 1994 [DE] Germany .............................. 9413576 U
Feb. 16, 1995 [DE] Germany .......................... 195 05 109.2
Feb. 16, 1995 [DE] Germany .......................... 195 05 110.6

[51] Int. Cl.$^6$ ................................ C10J 1/08; C12M 3/00
[52] U.S. Cl. ................................ 261/122.1; 435/297.2; 435/818; 422/48; 422/140; 210/321.78; 210/321.87; 210/321.88

[58] Field of Search ........................ 261/122.1; 422/48, 422/140; 435/297.1, 297.2, 295.3, 818; 210/321.72, 321.78, 640, 321.87, 321.88

[56] References Cited

U.S. PATENT DOCUMENTS

| 5,034,164 | 7/1991 | Semmens | 261/122 |
| 5,352,610 | 10/1994 | Braeutigam | 435/284 |
| 5,510,262 | 4/1996 | Stephanopoulos et al. | 435/240.23 |

FOREIGN PATENT DOCUMENTS 8703615  6/1987  WIPO .............................. C12M 3/00

*Primary Examiner*—David A. Redding
*Attorney, Agent, or Firm*—Herbert Dubno

[57] ABSTRACT

A cell culture reactor can have one or more gasification modules in which tubular membrane hoses surround rigid inner tubes which extend above the membranes to communicate with gas inlets or outlets. The tube is anchored in a closure member at the lower end of the membrane.

23 Claims, 3 Drawing Sheets

5,601,757

GASIFICATION-TUBE MODULE AND REACTOR FOR CELL CULTIVATION

FIELD OF THE INVENTION

Our present invention relates to a gasification (especially oxygenation) tube module for use with cell culturing reactors and, more particularly, to gasification tube modules with selective gas permeable tubular membranes and reactors provided with such modules for use in cell culture and especially for cell culturing systems operating as fluidized beds.

The invention is particularly directed to the gasification of a cell culture medium with such a module in such a reactor through a selective tubular membrane in a bubble-free transfer of gas to the liquid medium.

BACKGROUND OF THE INVENTION

In cell cultures, for example, to produce pharmacologically effective substances, the culturing of animal cells from which pharmacologically materials are recovered and generally wherever a cell culture is required, the ability to supply oxygen to the culture medium in a stress-free manner plays a very important role. It has been proposed for example, to supply oxygen in body to the system by diffusion of the oxygen through nonporous membranes, for instance materials based upon silicone rubber (see German Patent 24 31 450).

In German Patent 29 40 446, a fermenter is described for the culturing of animal cells in suspension or in a monolayer culture with internal liquid circulation utilizing a stirrer. The nutrient medium is supplied with oxygen through a membrane which is preferably composed of silicone rubber and is wound as a tube spirally on a carrier surface.

WO 87/03615 describes a process for supplying oxygen to a fermenter in a bubble-free manner utilizing a pore-free plastic membrane with integrated fabric reinforcement and which is supported in the fermenter on form-stable, e.g. rigid, support elements. This arrangement can be used in a stirred vessel or in a fluidized bed fermenter.

Dr. Bräutigam Membrantechnik in Hamburg, Germany produces glass-fiber reinforced membrane tubes which are mounted on stainless steel tubes as carriers and which can be pressurized to about 5 bar and are marketed as so-called self-supporting membrane candles. These membrane candles can be mounted between an upper and lower gas manifold and utilized in a reactor provided with a stirrer having a working volume of say 100 liters.

Such membrane filter candles are comparatively expensive and require connections at both their upper and lower ends to cooperate with the respective manifolds. The gas manifolds at the lower ends of the membrane filter candles are disposed at lower portions of the reactor vessel and can be an impediment to optimum flow distribution therein.

OBJECTS OF THE INVENTION

It is, therefore, the principal object of the present invention to provide a gasification module, especially for culture vessels of the type described, whereby drawbacks of earlier systems are obviated.

It is also an object of the invention to provide a culture vessel with improved gasification which will be less expensive and can be operated with reduced flow distribution impediments.

SUMMARY OF THE INVENTION

These objects and others which will become apparent hereinafter are attained, in accordance with the invention, with the aid of a tubular or hose-like membrane which is provided internally with a stiff axially-extending gas conducting tube having at least one opening communicating between the interior of this tube and the space surrounded by the tubular membrane at the lower end of the rigid tube. The connecting elements for the space surrounding the rigid tube and for the space within the rigid tube are formed at the top of the tubular gasification module thus formed and the connecting element for the inner passage of the rigid tube projects upwardly beyond the upper end of the tubular membrane and preferably its connecting fitting.

More particularly, the gasification module for bubble-free gasification of a culture medium in a cell culture reactor can comprise:

- a vertically elongated non-porous tubular membrane having an upper end and a lower end, the membrane being permeable to at least one component of a gas;
- a closure member at the bottom end closing communication with the tube from an exterior thereof;
- a slender shape-stable axially extending inner tube within the membrane and extending from the closure member at the lower end to the upper end, the membrane being spaced from the inner tube to form an outer passage, the inner tube having at least one opening—at least at the lower end—connecting the outer passage with the inside of the inner tube forming an inner passage; and
- means forming fittings at the upper end for connecting one of the passages to a source of gas and the other of the passages to a gas outlet, the fitting for the inner passage extending above the upper end of the tubular membrane.

Preferably the fitting for the inner passage can be connected to the gas outlet and the fitting for the outer passage can be connected to the gas source. The gasification module of the present invention is thus formed with a double tube construction with a direction change of the gas at the lower end so that the manifolds for supplying the gas to the modules and receiving gas from the module can be provided at the top of the reactor, preferably in the reactor head.

The rigid axial inner gas tube is stiff and can be fitted to the closure member of the tubular membrane, e.g. by being pressed onto it or into it, this closure member preferably being formed as a conical or substantially conical flow guide body. Alternatively or in addition, it can fit into a seat in a lower flow distribution bottom or plate of a fermenter, preferably operating in a fluidized bed mode.

The upper ends of the modules, especially when a comparatively large number are provided, can be anchored in the cover of the reactor or in a separate or integrated manifold system. The axial tube can be extended upwardly to form the fitting above the tubular membranes and this axial extension can be anchored in the manifold for discharging the gases. The connection to the manifold for supplying the gas to the modules can be accomplished by simply pressing the tubular membranes over appropriate fittings on the gas supply manifold.

For a fluidized bed reactor in which a single module is provided in a vessel of limited diameter to be operated in a fluidized bed technique and where the annular gap between the module and the vessel wall is say less than or equal to 12 mm, the module can be mounted in the reactor cover or can be integral therewith or integrated therein. The cover can thus have any requisite seals for effecting sealing with the reactor vessel and with the inner tube and tubular membrane and is also provided with the passages communicating with the membranes and with the inner tube. The cover can thus have a cap for the tubular membrane through which the extension of the inner tube passes. The end of the inner tube can terminate in a blow-off or venting fitting or in a manifold for collecting the discharged gas.

The tubular membranes which are used according to the invention can be comparatively thin but of course not as thin as production induced thickness fluctuations of the membrane would result in a perforation thereof under operation pressure. Membrane thicknesses of 0.4 to 0.8 mm and preferably 0.5 to 0.7 mm and a diameter of at least 1 cm are preferred.

Especially advantageous, are membrane tubes which are provided on the inside with a support of fabric which can lie in contact with the inner membrane surface but which are not embedded or incorporated in the membrane. The supporting fabric can be a glass-thread mesh or web with, for example, a thickness of about 1 mm which has been used in electrical insulating sheaths, as described, for example in German patent document DE 41 00 265 A1, although with silicone members of substantially greater wall thickness than are used in the present invention.

Of course, membranes with integrated fiber-reinforcement could be used if wanted, though these are not preferred.

The membrane can allow an oxygen supply to the system of up to 200 mg/l×h and more, for which purpose specific membrane areas of 30 to 150 $m^2/m^3$ of reactor volume are preferred.

The membrane hose or tubular membrane structure of the invention with an inside supporting web can be employed in lengths of up to 2 m and more and thus can be utilized for production reactors of various constructions and use types as are particularly advantageous for cell cultures.

Especially preferred are fluidized bed reactors in which the carriers are granulates on which the cells can be immobilized. High cell densities of say up to $10^8$/ml of carrier granulate can be achieved and thus the reactors for cell cultivation can be especially economical, even for large scale cultures.

The carrier bodies or granulates can be open-pore particles of relatively small size (preferably 0.4 to 1 mm diameter) with a specific weight in excess of 1 $g/cm^3$. The beads may be composed of inert glass or ceramic material although carrier bodies of synthetic or natural polymers may be used, especially if they are weighted. Especially preferred, however, are commercially available open-pore sintered glass beads of high porosity as marketed by the firm Schott of Mainz, Germany, under the trademark Siran®.

Advantageously the fluidized bed reactors in a technical scale have more than one membrane module disposed therein with the lower ends of the membrane modules being inserted or anchored in seats formed in a sieve bottom and complementary to the closure member at the bottom of the modules. The sieve bottom may be a sieve plate, a slitted plate (especially a parallel slit plate), a bell tray or the like. The carrier bodies are provided above the sieve bottom and the gas-collecting manifold can be provided above the top of the fluidized bed, i.e. above the boundary between the fluidized carrier bodies and a portion of the medium free from such bodies but thereabove.

When the carrier bodies are themselves very fine, the sieve bottom which serves to distribute the upwardly flowing medium through the fluidized bed can also have a finely perforated plate, a fine-mesh sieve or the like which can be located at the bottoms of the modules or below the latter.

The gasification modules of the invention have been found to be advantageous for cell proliferation, cultivation and other cell studies as well as pharmacological tests with mixed cell populations in a fluidized bed. For laboratory-scale use, the fluidized bed reactor with a single membrane tube module can be used.

In the case of the single module reactor, the bottom closure of the membrane module can be downwardly converging conical flow-guide member and the module can form an annular gap with the reactor wall of a width of 4 to 12 mm, the reactor wall being in turn thermostated. The biomass growth is detected on the carrier bodies which move in a fluidized bed in this gap fluidized by nutrient media supplied along the closure member. A recirculation path is provided for this medium which is drawn from the vessel above the fluidized bed and pumped back into the conical bottom of the vessel below the closure member. A fluidized bed reactor according to the invention thus can comprise:

an upright reactor vessel containing a cell cultivation medium;

means forming a medium recirculation path with the vessel and having an inlet for recirculated medium at the bottom of the vessel; and a gasification module for bubble-free gasification of the medium in the reactor, the gasification module comprising:

a vertically elongated non-porous tubular membrane having an upper end and a lower end, the membrane being permeable to at least one component of a gas (especially oxygen), a closure member at the bottom end closing communication with the tube from an exterior thereof, the closure member forming a flow guide for the medium conically converging toward the medium inlet, a slender shape-stable axially extending inner tube within the membrane and extending from the lower end to the upper end, the membrane being spaced from the inner tube to form an outer passage, the inner tube having an opening at the lower end communicating between the outer passage and the inside of the inner tube forming an inner passage, and means forming fittings at the upper end for connecting one of the passages to a source of gas and the other of the passages to a gas outlet, the fitting for the inner passage extending above the upper end of the tubular membrane.

Preferably the inner tube is fixed or anchored within the lower closure member of the membrane module.

The membrane in the most general terms can have a thickness of 0.3 to 1 mm. The carrier bodies can have diameters of 200 and 700 μm, pore sizes of 20 to 100 μm and the bulk volume of the carriers can amount to perhaps 40% of the working volume of the reactor inclusive of the recirculation path. Especially for cell research the working volume of the reactor inclusive of the recirculation path preferably amounts to at most 100 ml, the bulk volume of the carriers being between 0.2 and 0.6 times the working volume and is composed of glass particles of diameters of at most 1000 μm and a porosity of about 50%.

The fluidized bed reactor can have a sterile sampling system formed on the reactor for withdrawing carrier samples.

Alternatively the cell cultivation reactor can comprise:

an upright reactor vessel containing a cell cultivation medium;

a multiplicity of horizontally spaced apart mutually parallel vertical gasification modules for bubble-free gasification of the medium in the reactor, each of the gasification modules comprising:
  a vertically elongated non-porous tubular membrane having an upper end and a lower end, the membrane being permeable to at least one component of a gas,
  a closure member at the bottom end closing communication with the tube from an exterior thereof, the closure member forming a flow guide for the medium conically converging toward the inlet,
  a slender shape-stable axially extending inner tube within the membrane and extending from the lower end to the upper end, the membrane being spaced from the inner tube to form an outer passage, the inner tube having an opening at the lower end for communicating between the outer passage and the inside of the inner tube forming an inner passage, and
  means forming fittings at the upper end for connecting one of the passages to a source of gas and the other of the passages to a gas outlet, the fitting for the inner passage extending above the upper end of the tubular membrane;
a manifold at the upper ends of the modules connected to the fittings of the one passages for connecting same to the source and another manifold connected to the fittings of the others of the passages for discharging gas; and
means in the reactor at the lower ends of the modules for anchoring the closure members of the modules.

In the latter case, the vessel can have a height of at least 0.5 m for cell culture with a density of at least $10^7$ cells/ml of medium, the membrane having a thickness of at most 0.8 mm and a gas pressure of at most 1 bar above the hydrostatic pressure of the medium is used to pressurize the membrane tube modules.

As a general matter the membrane may have an area of 30 to 150 $m^2$ per $m^3$ of contents of the reactor. The gas charging the tubular membranes should be at a pressure of at least 0.5 bar above the hydrostatic pressure of the surrounding medium.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
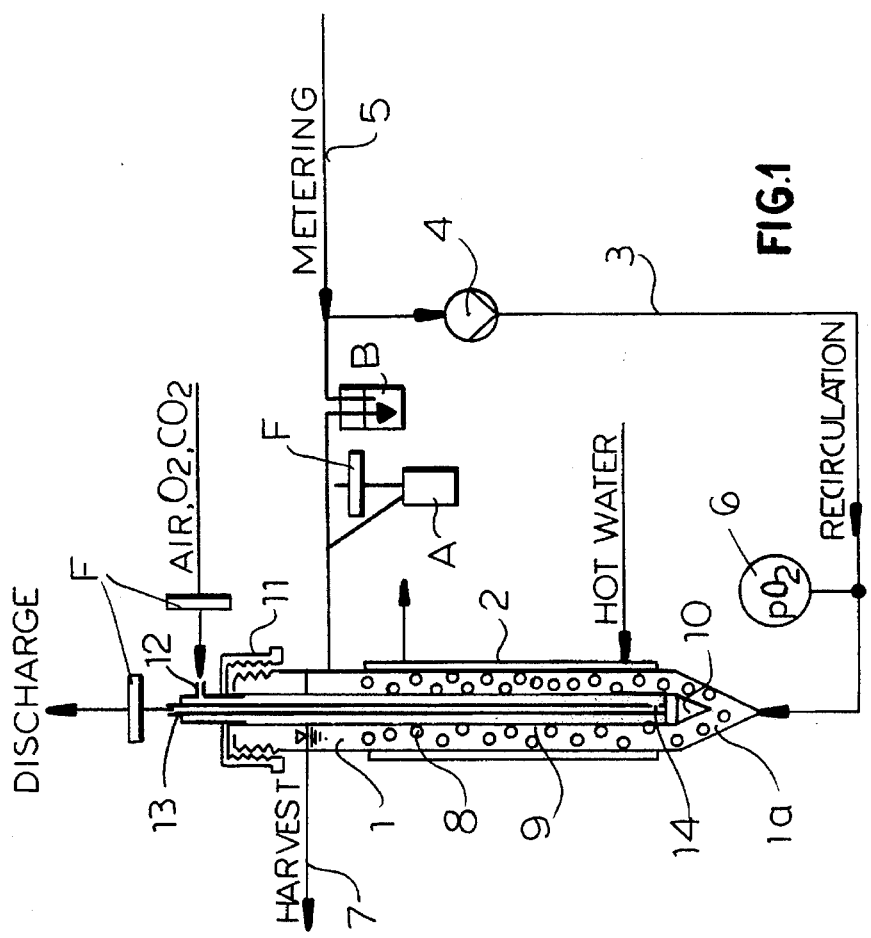
FIG. 1 is a cross sectional view through a fluidized bed reactor in accordance with the invention.

The apparatus shown in FIG. 1 has been found to be suitable for cell research and development and can be provided on a relatively small scale with working volumes including the recirculating path of a maximum of 100 ml. For specific pharmacological production, the vessel of FIG. 1 having a single gasification tube module may be increased and additionally can have an increased membrane diameter, for up-scaling and providing high aeration rates.

As can be seen from FIG. 1, the generally cylindrical reactor vessel 1 can be provided with a heating jacket 2 and a recycling path 3 for the liquid nutrient medium circulated by peristaltic pump 4.

A metering unit represented at 5 can dose the liquid medium and desired substances to be investigated, especially for the effect on the cell culture, into the circulating nutrient medium. The medium itself maybe monitored for a variety of parameters, especially the oxygen partial pressure as represented by the oxygen detector 6 along the recirculating path.

At 7, the reactor medium can be withdrawn, e.g. via an overflow. Supply and withdrawal can also be integrated in the circulating path or in the reactor as may be desired.

The medium is introduced through the conical bottom 1a of the vessel which contains a fluidized bed of carrier beads on which the cells can be immobilized. Fluidization is effected by the upward flow and because of the relatively high specific gravity of the carrier beads, the latter remain in the vessel and do not pass over the overflow with the harvested nutrient medium.

Within the cylindrical tube forming the reactor vessel, a gasification module 9 is provided with a tubular silicone member through which oxygen is supplied for the cell culture.

In the embodiment shown, the reactor can have a total working volume (including recirculation) of 60 ml and a carrier bulk volume of 20 ml. The membrane of the gasification module has a thickness of 0.5 mm and is closed at its lower end by a downwardly converging conical closure member 10 which acts as a guide for the upwardly flowing liquid medium. The downward taper of the vessel has a diameter at its lower end of that of the recirculating tubing (less than 7.5 mm). The reactor tube has a diameter of 16 mm and at its upper end is closed by a cap 11 through which the gasification tube module 9 passes, the latter being provided above the cap 11 with a feed fitting 12 for the gas which can open into the space around the rigid axial tube 13 and within the tubular membrane.

The upper end of the rigid tube 13 extends above the tubular membrane and discharges air through a filter F. The supplied gas also passes through a filter F prior to being admitted to the fitting 12.

The axial tube 13 engages in the closure member 10 in which it can be force-fitted or to which it can be welded. Above the closure member 10 but at the lower end of the rigid tube 13, the latter can be provided with an opening 14 communicating between the space between the membrane and the axial rigid tube and the passage through the latter.

Because of the opening 14 at the lower end of the module, condensate which may accumulate in the module can be carried off with the returning gas stream.

The circulating path can have a T fitting connected to a medium sampling vessel A vented via a filter F and which, after filling, can be sterilely sealed by a flame or sterilely replaced by another collection vessel. For removing samples of the carrier, a carrier trap B can be provided in the circulation. For sampling of the carrier, the speed of the pump is temporarily increased to entrain some of the carrier particles in the circulation and to enable them to be trapped in the vessel B. All of the filters F are sterilization filters.

Figure 2:
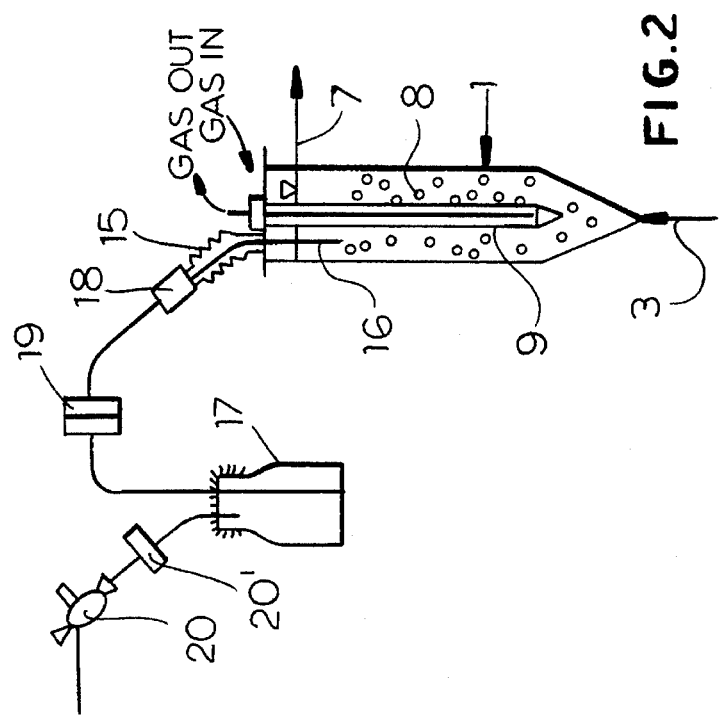
FIG. 2 is a view similar to FIG. 1 of a reactor provided with a sampling system different from that of FIG. 1.

FIG. 2 shows a system generally similar to that of FIG. 1 but wherein carrier sampling is effected via a bellows 15 of variable length (e.g. 12 to 23 cm) in which a Teflon tube 16 is provided. In the expanded state of the bellows, the Teflon tube is disposed above the reactor medium in the head of the reactor tube. Thus the Teflon tube 16 does not interfere with the flow characteristics of the reactor. When the Teflon tube is advanced, with contraction of the bellows, the Teflon tube can dip into the fluidized bed a shown. In this position, suction applied through the flask 17 can draw a sample of the medium and the carrier bodies into the flask while maintaining the sterile state.

The connection between the bellows 15 and the flask 17 can draw a sample of the medium and the carrier bodies into the flask while maintaining the sterile state.

The connection between the bellows 15 and the flask 17 may be a flexible stainless steel tubing to which the bellows 15 is connected by the clamping screw assembly 18 and which can be provided with a sterile coupling. The flask 17 can be connected via a sterile filter 20' to a Peleus ball 20 for the suction of samples. Via the Peleus ball valve, medium and carrier residues in the tubing can be blown back into the reactor by superatmospheric pressure. The system 15–20 thus allows sterile sampling of the reactor of FIG. 2 which is otherwise similar to that of FIG. 1.

Figure 3:
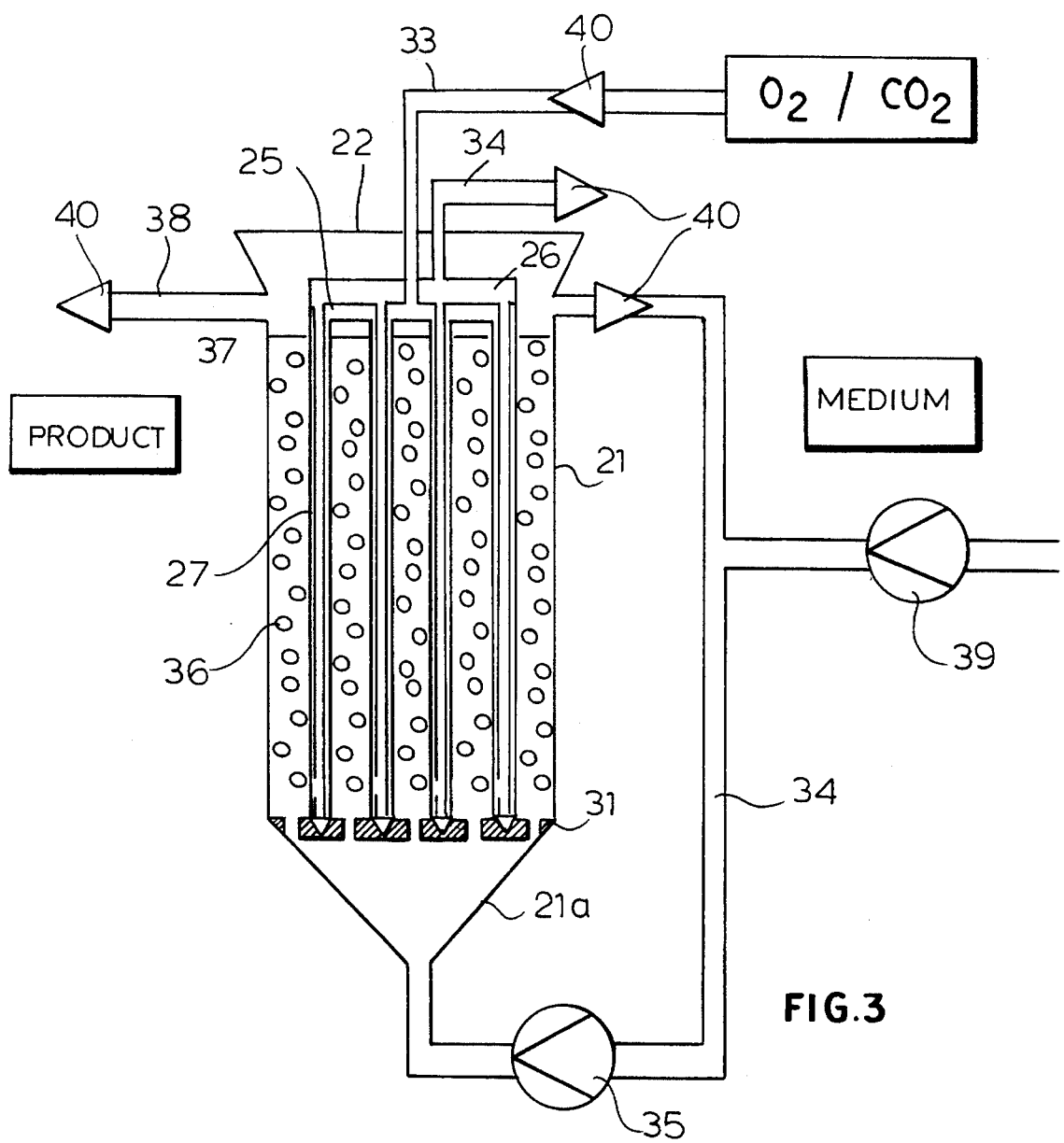
FIG. 3 is a cross sectional view through a fluidized bed reactor utilizing a multiplicity of gasification modules of the invention.

FIG. 3 shows a fluidized bed reactor with a multiplicity of gasification tube modules according to the invention. As can be seen from FIG. 3, the substantially cylindrical vessel 21 has a removable (not shown) cover 22 through which the gas feed and discharge lines 23 and 24 can extend.

The top of the reactor is provided with a gas distribution manifold 25 and a gas collection manifold 26 through which respectively the gas (air, oxygen-enriched air and optionally carbon dioxide in the start-up phase) can be introduced into the gasification modules 27 and discharged therefrom.

Each of the gasification tube modules 27 comprises an outer membrane tube or hose 28 with an internal supporting fabric 29 of glass fiber mesh of a thickness of about 1 mm. The lower ends of the membranes 28 are closed by closure members 30 with a conical outer contour and seated in complementary recesses of a sieve bottom 31 delimiting the bottom of the fluidized bed space and serving as a flow distributor for the medium introduced through the conical bottom 21a of the reactor.

Figure 3A:
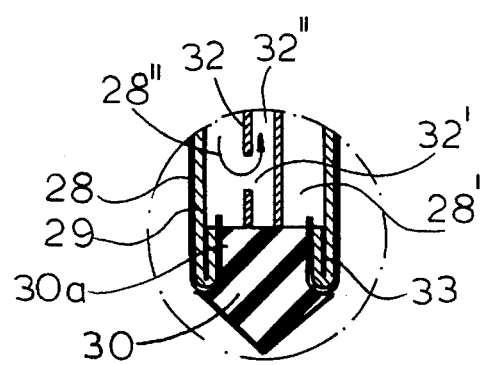
FIG. 3A is a detail of the closed end of the gasification module.

In the closure member 30 a stainless steel inner tube 32 is fixed, this rigid tube running through an entire module. At its lower end it is provided with an opening 32' having a diameter of e.g. at least 2.0 mm and connecting the compartment 28' inwardly of the membrane 28 with a passage 32" extending through the inner tube (FIG. 3A).

The passages 32" communicate with the collecting manifold 26 above the membranes 28.

Of course, the flow direction of the oxygen-containing gas through the membrane modules can be selected at will, i.e. in the opposite direction from that represented by the arrow 28", but it has been found to be most advantageous to discharge the gas through the comparatively narrow axial tubes 32 and to introduce the gas through the outer compartments 28' since this ensures that the inner surfaces of the membrane will remain dry.

The axial tubes 32 also maintain the mechanical integrity of the modules since they support the membranes without rigid supporting structures against which the membranes must lie. Ideally the axial tubes are composed of V4A stainless steel with an inner diameter of at least 2 mm and a wall thickness of at least 1 mm for membrane diameters of at least 1 cm.

As can be seen from FIG. 3A, the membrane can be turned inwardly at its lower end to form a bead which is fitted over a boss 30a of the closure member 30, with a press fit. In this case the silicone foil also acts as an internal sealing against the closure member.

The reactor comprises a recycling tube 34 provided with a medium pump 35 capable of generating the velocity of medium necessary to hold the carrier bodies 36 in suspension and maintain an equilibrium between the sedimentation and entrainment forces on these particles. The result is a stable fluidized bed with a discrete boundary 37 above which the product can be decanted at the upper end via an overflow 38. The arrows 40 indicate the flow direction.

The carrier bodies are preferably open-pore Siran® beads with a porosity of 50% and composed of borosilicate glass with diameters of 400 to 700 µm. The gas is fed at 23 at a pressure which is a maximum of 1 bar above the hydrostatic pressure in the reactor and preferably is not more than 0.5 bar above the hydrostatic pressure. The upper connections of the membrane modules to the manifold can be permanent or releasable and advantageously the type of connection used to the closure member 30 can be provided between the upper ends of the membranes and manifold fittings.

Figure 4:
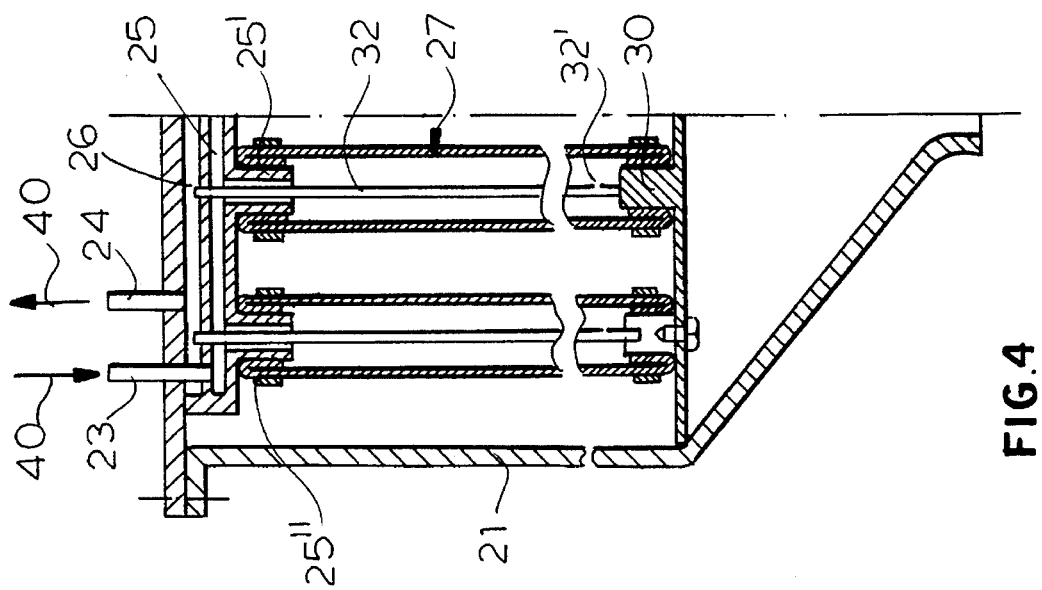
FIG. 4 is a cross sectional view through a portion of another reactor in accordance with the invention.

FIG. 4 shows gas distribution and collection manifolds 25, 26 integrated onto a removable cover 22. The membrane tubes 27 are held by fixing bands 25" to clamp these membrane tubes onto fittings 25' of the manifold 25. Other types of connections such as clamp systems or the like may be used. The upper ends of the tubes 32 may be tightly fixed to the bottom of the gas collection manifold 26, e.g. by welding or releasable connected e.g. sealingly screwed.

The lower closure member 30 is here shown to be integrated into the lower mounting support which may be different (or not) from a flow distribution plate at the lower end of the fluidized bed reactor. This support can be a Teflon grid or perforated Teflon plate. Beneath the support, sieve bottoms (not shown) can be used at the bottom of the fluidized bed reactor as well, including bell tray bottoms, inverted trough bottoms or fine-sieve bottoms.

Figure 5:
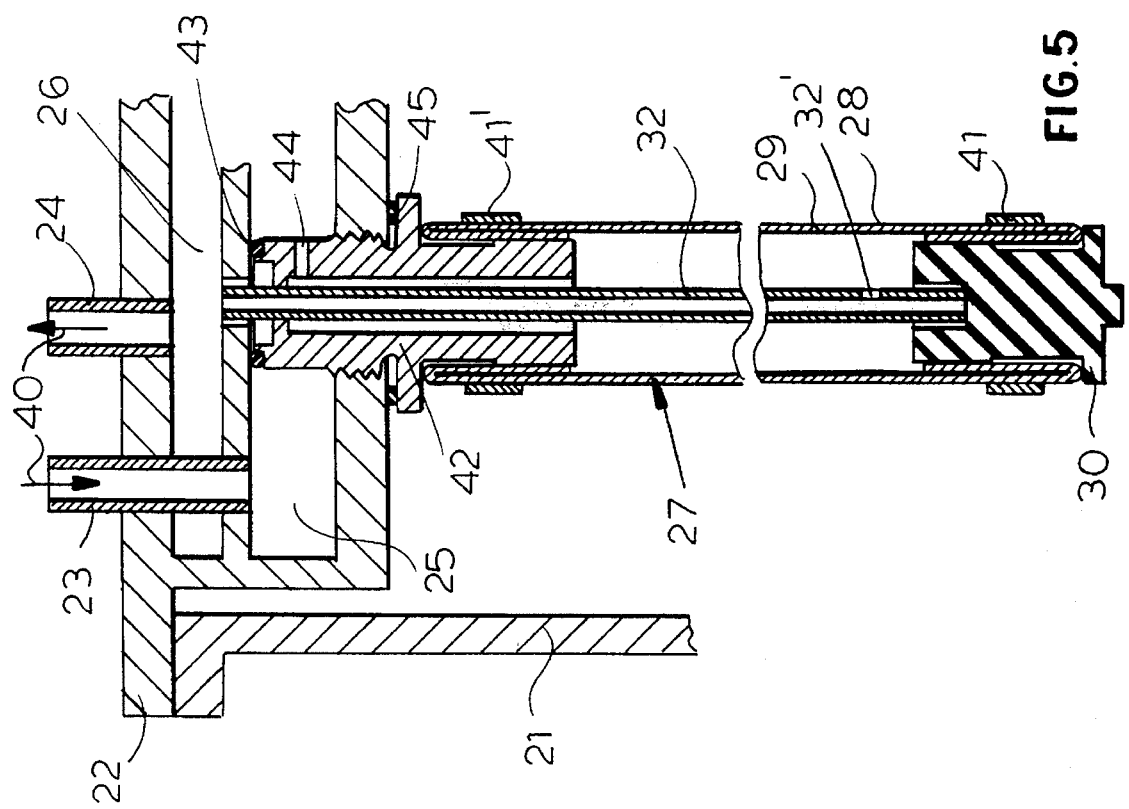
FIG. 5 is a detail drawn to an enlarged scale of FIG. 4.

FIG. 5 shows a reactor generally similar to FIG. 4 and even having elements similar to FIG. 3 as indicated by the use of similar reference numerals in FIG. 5, however, the tubes 23 and 24 are shown to be welded into a removable reactor cover 22 in which the manifolds 25 and 26 are integrated. The lower closure member 30 of each module has a pin for indexing it in the support or flow distributing bottom and the membrane 28 is supported by the fabric 29 and is secured by clamping rings 41 to the closure fittings 30 and to fittings 42 which are threaded into the manifold 25. The fittings 42 have passages 44 communicating with the space surrounding the rigid tube 32 and seals 43 and 45 can provide sealing between the fitting 42 and the manifolds 25 and 26.

We claim:

1. A gasification module for bubble-free gasification of a culture medium in a cell culture reactor, said gasification module comprising:

a vertically elongated non-porous tubular membrane having an upper end and a lower end, said membrane being permeable to at least one component of a gas;

a closure member at said lower end closing said membrane tube from an exterior thereof;

a shape-stable axially extending inner tube within said membrane and extending from said closure member of said lower end to said upper end, said membrane being spaced from said inner tube to form an outer passage, said inner tube having an opening at said lower end connecting said outer passage with the inside of said inner tube forming an inner passage; and means forming fittings at said upper end for connecting one of said passages to a source of gas and the other of said passages to a gas outlet, said fitting for the inner passage extending above the upper end of said tubular membrane.

2. The gasification module defined in claim 1 wherein said fitting for said inner passage is connectable to a gas outlet and said fitting for said outer passage is connectable to a gas source.

3. The gasification module defined in claim 1, further comprising a flexible support fabric in contact with the inner side of said membrane.

4. The gasification module defined in claim 1 wherein said fittings are built into a cover for said reactor.

5. The gasification module defined in claim 1 wherein said closure member has a downwardly tapering conical configuration and forms a fluid flow guide.

6. The gasification module defined in claim 1 wherein said closure member for said membrane tube matches with a receiving contour of a supporting element of the fermenter.

7. The gasification module defined in claim 1 wherein said membrane has a thickness of 0.3 to 1 mm.

8. The gasification module defined in claim 1 wherein said tubular membrane has a diameter of $\geq 1$ cm.

9. The gasification module defined in claim 1 wherein said tubular membrane is composed of a silicone-base material.

10. A fluidized bed cell cultivation reactor, comprising:

an upright reactor vessel for containing a cell cultivation medium;

means forming a medium recirculation path with said vessel and having a inlet for recirculated medium at a bottom of said vessel; and a gasification module for bubble-free gasification of the medium in said reactor, said gasification module comprising:

a vertically elongated non-porous tubular membrane having an upper end and a lower end, said membrane being permeable to at least one component of a gas, a closure member at said lower end closing said membrane tube from an exterior thereof, said closure member forming a flow guide for said medium conically converging toward said inlet, a shape-stable axially extending inner tube within said membrane and extending from said lower end to said upper end, said membrane being spaced from said inner tube to form an outer passage, said inner tube having an opening at said lower end connecting said outer passage with the inside of said inner tube forming an inner passage, and means forming fittings at said upper end for connecting one of said passages to a source of gas and the other of said passages to a gas outlet, said fitting for the inner passage extending above the upper end of said tubular membrane.

11. The fluidized bed cell cultivation reactor defined in claim 10, further comprising a connection of the lower end of said axial tube with said closure member.

12. The fluidized bed cell cultivation reactor defined in claim 10, further comprising a cover removably mounted on said vessel, said gasification module being fixed in said cover.

13. The fluidized bed cell cultivation reactor defined in claim 10, further comprising open-pore glass carriers in said vessel for immobilization of cultivated cells.

14. The fluidized bed cell cultivation reactor defined in claim 13 wherein said carriers have a diameter of 200 to 700 µm.

15. The fluidized bed cell cultivation reactor defined in claim 13 wherein said carriers have a pore size of 20 to 100 µm.

16. The fluidized bed cell cultivation reactor defined in claim 13 wherein the bulk volume of said carriers amounts to about 40% of the working volume of said reactor inclusive of said recirculation path.

17. The fluidized bed cell cultivation reactor defined in claim 13 wherein said reactor inclusive of said recirculation path has a working volume of $\leq 100$ ml, said bulk volume of said carriers amounts to between 0.2 and 0.6 times the working volume, and said carriers are formed by glass particles of diameters $\leq 1000$ µm, a pore size $\leq 100$ µm and a porosity of about 50%.

18. The fluidized bed cell cultivation reactor defined in claim 13, further comprising a sterile sampling system formed on the reactor for withdrawing carrier samples.

19. A cell cultivation reactor, comprising:

an upright reactor vessel for containing a cell cultivation medium;

a multiplicity of horizontally spaced apart mutually parallel vertical gasification modules for bubble-free gasification of the medium in said reactor, each of said gasification modules comprising:

a vertically elongated non-porous tubular membrane having an upper end and a lower end, said membrane being permeable to at least one component of a gas, a closure member at said bottom end closing communication with said tube from an exterior thereof, said closure member forming a flow guide for an upwardly streaming medium at the reactor bottom, a shape-stable axially extending inner tube within said membrane and extending from said closure member to said upper end, said membrane being spaced from said inner tube to form an outer passage, said inner tube having an opening at said lower end communicating between said chamber and an inner passage of said inner tube, and means forming fittings at said upper end for connecting one of said passages to a source of gas and the other of said passages to a gas outlet, said fitting for the inner passage extending above the upper end of said tubular membrane;

a manifold at said upper ends of said modules connected to the fittings of said one passages for connecting same to said source and another manifold connected to the fittings of said others of said passages for discharging gas; and means in said reactor at said lower ends of said modules for anchoring said closure members of said modules.

20. The reactor defined in claim 19, further comprising granular carrier bodies for immobilizing cells cultured in said vessel, and means for fluidizing contents of said vessel to form a fluidized bed therein.

21. The reactor defined in claim 20 wherein said vessel has a height of $\geq 0.5$ m for cell culture with a density of $\geq 10^7$ cells/ml of said medium, said membrane having a thickness of $\leq 0.8$ mm, a diameter of $\geq 1$ cm and a flexible fabric in contact with the inner side of the membrane and being pressurized with a gas pressure which is $\leq 1$ bar above a hydrostatic pressure of surrounding medium.

22. The reactor defined in claim 21 wherein said membrane has an area of 30 to 150 mm$^2$/m$^3$ of contents of the reactor.

23. The reactor defined in claim 21, further comprising means for charging said tubular membranes with gas at about $\leq 0.5$ bar above a hydrostatic pressure of surrounding medium.

* * * * *